United States Patent
Zhang et al.

(10) Patent No.: US 12,077,749 B2
(45) Date of Patent: Sep. 3, 2024

(54) ***BIFIDOBACTERIUM LONGUM* SUBSP. *INFANTIS* WITH FIMBRIAE AND APPLICATIONS THEREOF**

(71) Applicant: Northeast Agricultural University, Harbin (CN)

(72) Inventors: Lili Zhang, Harbin (CN); Hui Sun, Harbin (CN); Zihe Xu, Harbin (CN); Ze Tan, Harbin (CN); Lihong Xiao, Harbin (CN); Mingxue He, Harbin (CN)

(73) Assignee: Northeast Agricultural University, Harbin (CN)

( * ) Notice: Subject to any disclaimer, the term of this patent is extended or adjusted under 35 U.S.C. 154(b) by 0 days.

(21) Appl. No.: 18/241,009

(22) Filed: Aug. 31, 2023

(65) Prior Publication Data

US 2024/0182847 A1    Jun. 6, 2024

(30) Foreign Application Priority Data

Oct. 20, 2022  (CN) .......................... 202211286087.4

(51) Int. Cl.
| | | |
|---|---|---|
| *C12N 1/20* | (2006.01) | |
| *A61K 35/00* | (2006.01) | |
| *A61K 35/745* | (2015.01) | |
| *C12R 1/01* | (2006.01) | |

(52) U.S. Cl.
CPC ............ *C12N 1/205* (2021.05); *A61K 35/745* (2013.01); *A61K 2035/115* (2013.01); *C12R 2001/01* (2021.05)

(58) Field of Classification Search
CPC .. C12N 1/205; C12R 2001/01; A61K 35/745; A61K 2035/115
See application file for complete search history.

(56) References Cited

U.S. PATENT DOCUMENTS 5,711,977 A    1/1998   Yang et al.

FOREIGN PATENT DOCUMENTS

| CN | 105112333 A | 12/2015 |
|---|---|---|
| CN | 106715680 A | 5/2017 |
| CN | 113773983 A | 12/2021 |
| CN | 113841898 A | 12/2021 |

OTHER PUBLICATIONS

Foroni et al., "Genetic analysis and morphological identification of pilus-like structures in members of the genus *Bifidobacterium*", Microb Cell Fact 10 (Suppl 1), S16 (2011). https://doi.org/10.1186/1475-2859-10-S1-S16 (Year: 2011).*

Guan et al., Screening for and Biological Characterization of Bifidobacterium infantis Capable of Promoting Proliferation of Human Fetal Colon Epithelial Cells, Food Science, 2021, 42(18): 86-94. (in Chinese with English abstract) DOI:10.7506/spkx1002-6630-20200914-179, pp. 86-94.

Munoz et al., Novel Probiotic Bifidobacterium longum subsp. *infantis* CECT 7210 Strain Active against Rotavirus Infections, Applied and Environmental Microbiology, Dec. 2011, vol. 77, No. 24, p. 8775-8783.

Zhao et al., (2021) Identification, Characterization, and Antioxidant Potential of Bifidobacterium longum subsp. *longum* Strains Isolated From Feces of Healthy Infants. Front. Microbiol. 12:756519.doi: 10.3389/fmicb.2021.756519, 13 pages.

Guan et al. Characteristics and Application of Bifidobacterium longum[J]. Science and Technology of Food Industry, 2021, 42(12): 430-438. (in Chinese with English abstract). doi: 10.13386/j.issn1002-0306.2020070121, 9 pages.

Chichlowski et al., Bifidobacteria isolated from infants and cultured on human milk oligosaccharides affect intestinal epithelial function, J Pediatr Gastroenterol Nutr. Sep. 2012 ; 55(3): 321-327. doi:10.1097/MPG.0b013e31824fb899, 17 pages.

CNIPA in application No. 2022112860874 and its English translation thereof; pp. 1-29.

Maciej Chichlowski, Ph.D, et al; "Bifidobacteria isolated from infants and cultured on human milk oligosaccharides affect intestinal epithelial function"; J Pediatr Gastroenterol Nutr. Sep. 2012 ; 55(3): pp. 321-327.

Li Zhao et al; "Identification, Characterization, and Antioxidant Potential of Bifidobacterium longum subsp. *longum* Strains Isolated From Feces of Healthy Infants"; Original Research: Nov. 2, 2021; pp. 1-13.

Guan Jiaqi; "Characteristics and Application of Bifidobacterium longum"; Science and Technology of Food Industry; vol. 42 No. 12; Jun. 2021; pp. 1-9.

Jose' Antonio Moreno Munoz et al; "Novel Probiotic Bifidobacterium longum subsp. *infantis* CECT 7210 Strain Active against Rotavirus Infections"; Applied and Environmental Microbiology, vol. 77, No. 24, Dec. 2011, pp. 8775-8783.

(Continued)

*Primary Examiner* — Ruth A Davis
(74) *Attorney, Agent, or Firm* — JCIPRNET

(57) ABSTRACT

A strain of *Bifidobacterium longum* subsp. *infantis* Y46 with fimbriae (BI_Y46) includes a unique flagella structure, exhibits strong abilities in utilizing 2'-fucosyllactose (2'-FL), galacto-oligosaccharides and short-chain galacto-oligosaccharides, possesses excellent probiotic characteristics with higher levels of extracellular polysaccharides and surface proteins than a strain of *Bifidobacterium longum* subsp. *infantis* M63 (BI_M63) and a strain of *Bifidobacterium longum* subsp. *infantis* ATCC 15697 (BI_15697), and further displays stronger ability to tolerate gastric acid and inhibitory ability of the cell-free supernatant to *Escherichia coli* ATCC 15922 than the BI_15697. Therefore, the BI_Y46 has excellent probiotic potential and can be used to develop probiotics, infant food, prebiotic products, and functional foods.

1 Claim, 1 Drawing Sheet
Specification includes a Sequence Listing.

(56) References Cited

OTHER PUBLICATIONS

Guan Jiaqi; "Screening for and Biological Characterization of *Bifidobacterium infantis* Capable of Promoting Proliferation of Human Fetal Colon Epithelial Cells"; Biological Engineering; vol. 42, No. 18, 2021, pp. 86-94.

* cited by examiner

BIFIDOBACTERIUM LONGUM SUBSP. INFANTIS WITH FIMBRIAE AND APPLICATIONS THEREOF

REFERENCE TO AN ELECTRONIC SEQUENCE LISTING

The contents of the electronic sequence listing (2023-11-07 Substitute Sequence Listing.xml; Size: 0.3593 bytes; and Date of Creation: Nov. 7, 2023) is herein incorporated by reference in its entirety.

TECHNICAL FIELD

The present invention belongs to the technical field of microorganisms, in particular to a strain of *Bifidobacterium longum* subsp. *infantis* with fimbriae and applications thereof.

BACKGROUND TECHNOLOGY

Bifidobacteria are mostly isolated from feces of infants and extremely important gut microbes closely associated with intestinal health. Bifidobacteria can not only promote the growth and development of the body, inhibit tumors and aging, but also regulate intestinal dynamic homeostasis, promote integrity of the intestinal barrier, alleviate symptoms of colitis, and enhance the immunity. Meanwhile, Bifidobacteria can use dietary sources and carbohydrates in the host's gut to boost the metabolism of the host. Bifidobacteria, as important probiotic supplements, have enormous market potential. However, the widely used bifidobacterial strains in the market are mainly well-known foreign strains such as *Bifidobacterium longum* BB536 and *Bifidobacterium longum* NCC2705, *Bifidobacterium longum* subsp. *infantis* M-63, and animal-derived *Bifidobacterium lactis* subsp. BB-12, HN019, and BI-017. In contrast, China has limited resources of "star strains" with excellent probiotic functions (Hu, Lujun, Jiangnan University 2017).

Most of bifidobacteria are in the shape of straight rods, rarely exhibit branching or curved forms, and only a few bifidobacteria possess fimbrial structures. Fimbriae are hair-like appendages that are contributive to the adhesion and colonization of human microbiota members to host tissues, facilitating a tighter bond between bacterial strains and host cell surfaces, allowing tighter binding between strains and host cell surfaces, while also reducing competition for attachment sites among related *bifidobacterium* species. Some strains of bifidobacteria require the involvement of flagella in biofilm formation. However, currently, the resources of bifidobacteria with flagella structures are quite limited.

Galacto-oligosaccharides (GOS) are oligosaccharides that are abundant in human milk, which possess strong resistance to digestion in the proximal gastrointestinal tract, and can promote colonization of bifidobacteria, enhance lipid metabolism, protect the liver and prevent colorectal cancer, etc. At present, commercial GOS products contain a lot of monosaccharides and various other disaccharides including lactose. There are significant differences in terms of linkage types and polymerization degree among GOS products offered by different suppliers. Studies have shown that short-chain galacto-oligosaccharides (SC-GOS) without monosaccharides and disaccharides exhibit excellent probiotic functionality, which can regulate the composition of intestinal microorganisms, increase the abundance of *bifidobacterium*, and improve lactose intolerance, etc. (Azcarate-Peril M Andrea et al., *Proceedings of the National Academy of Sciences of the United States of America*, 2017, 114(3): E367-E375).

2'-Fucosyllactose (2'-FL) is an important component of human milk oligosaccharides. Currently, several foreign dairy companies have started adding 2'-fucosyllactose to infant formula milk powder in order to narrow the gap between infant formula and breast milk. 2'-fucosyllactose has the ability to regulate the balance of gut microbiota, maintain intestinal health, promote the development of the immune system, and help prevent allergic diseases and inhibit the binding of pathogenic bacteria to the intestinal mucosa, thus reducing the occurrence of diarrhea. Additionally, 2'-fucosyllactose plays a role in brain development, neuronal transmission, and synapse formation, promoting brain development and improving learning and memory abilities.

Taskwan et al. (Taksawan T, L H J, Jornay C, et al. Journal of agricultural and food chemistry, 2017, 65(20): 4184-4192) analyzed the oligosaccharides utilization capacity of both bifidobacteria and *lactobacillus* bacteria, and found that *Bifidobacterium longum* subsp. *infantis* M-63 and *Bifidobacterium longum* subsp. *infantis* ATCC 15697 can effectively utilize short-chain galacto-oligosaccharides, and furthermore can maintain gut health by improving gut microbiota and intestinal environment. (Ishizeki S, Sugita M, Takata M, et al. *Anaerobe*, 2013, 23: 38-44.)

Currently, galacto-oligosaccharides are widely used in infant formula powder in China. Moreover, human milk oligosaccharides (HMOs) are regulated as "nutritional fortifiers" under food additive category in China. Formula milk powder and probiotic products containing HMOs from foreign countries have entered the domestic market and gained popularity among consumers. However, in China, there is limited research on bifidobacteria utilizing 2'-fucosyllactose and short-chain galacto-oligosaccharides. The strain resources are relatively scarce, and related products have not been effectively developed.

Therefore, the present invention aims to isolate and screen *bifidobacterium* strains from feces of infants that can efficiently utilize 2'-fucosyllactose, galacto-oligosaccharides, and short-chain galacto-oligosaccharides, employ genetic sequencing technology to determine species of selected strains, and evaluate extracellular polysaccharide contents, surface protein contents, self-aggregation ability, tolerance to simulated gastric fluid and bile salts, as well as antimicrobial activity in the supernatant, so as to obtain *bifidobacterium* strains with excellent probiotic characteristics, thus providing strain resources for product development.

SUMMARY OF THE INVENTION

The present invention provides a strain of *Bifidobacterium longum* subsp. *infantis* Y46 with fimbriae (abbreviated to, BI_Y46) deposited in China Center of Type Culture Preservation, in Wuhan, China, with a preservation number of CCTCC NO: M 20221253, dated Aug. 9, 2022.

Strain characteristics: scanning electron microscopy reveals that the BI_Y46 has a Y-shaped morphology, with presence of flagella on surfaces of cells.

The Omega D4015-01 Bacterial Genomic DNA Extraction Kit from Omega Bio-Tek was used to extract bacterial genomic DNA.

The mentioned strain exhibited a strong ability to utilize glucose and lactose and particularly exceled in utilizing 2'-fucosyllactose, galacto-oligosaccharides, and short-chain galacto-oligosaccharides.

The strain displayed significant resistance to bile salt stress, and had significantly higher levels of extracellular polysaccharides, surface protein content, self-aggregation ability, and the ability to adhere to intestinal epithelial cells compared to control strains.

Therefore, the mentioned strain can be used in food additives, probiotic products, synbiotics, yogurt, beverages, and other food applications.

The mentioned strain of *Bifidobacterium longum* subsp. *infantis* Y46 with fimbriae (BI_Y46) is also capable of inhibiting harmful bacteria, suppressing intestinal putrefaction, purifying the intestinal environment, breaking down carcinogenic substances, and stimulating the immune system, so as to help improve the body's disease resistance, particularly in inhibiting intestinal diseases. Thus, the strain can be used in the preparation of drugs that inhibit intestinal putrefaction, purify the intestinal environment, break down carcinogens, and stimulate the immune system, especially can be used in drugs related to the treatment of intestinal disorders.

The present invention has following beneficial effects:

The present invention provides a strain of *Bifidobacterium longum* subsp. *infantis* Y46 with fimbriae (BI_Y46), which possesses a unique flagella structure, exhibits strong capabilities in utilizing 2'-fucosyllactose, galacto-oligosaccharides and short-chain oligosaccharides, along with excellent probiotic characteristics. The strain of the present invention has higher levels of extracellular polysaccharides and surface proteins, as well as strong self-aggregation ability, tolerance to 0.2% pig bile salts, and adhesion to intestinal epithelial cells compared to BI_M63 and BI_15697. Additionally, the strain of the present invention demonstrates superior tolerance to gastric acid and greater inhibitory effects on *Escherichia coli* ATCC 15922 in cell-free supernatants compared to BI_15697. Therefore, the BI_Y46 of the present invention exhibits promising probiotic potential, provides a valuable reference for the development of probiotics, infant food, and prebiotic products, and also serves as a valuable strain resource for future research endeavors.

SPECIFIC EMBODIMENTS

Figure 1:
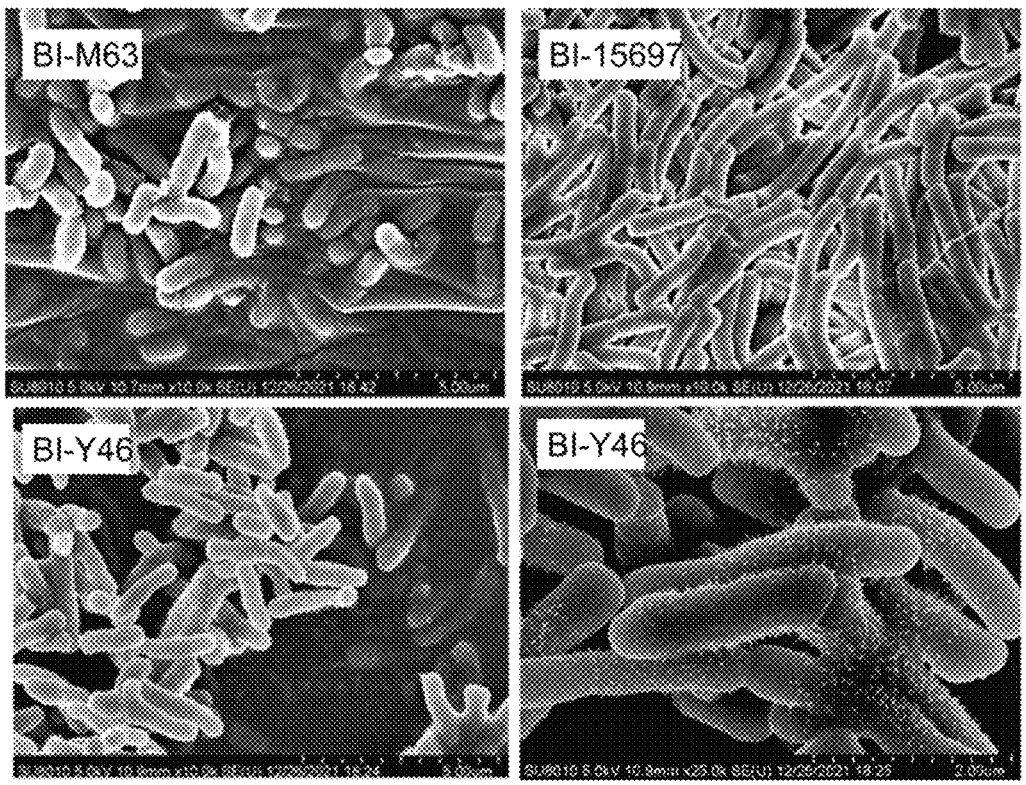
FIG. 1 shows morphology of strains.

The present invention is further elaborated in combination with specific embodiments and attached drawings.

*Bifidobacterium longum* subsp. *infantis* M63 (BI_M63) is a strain preserved in the laboratory. *Bifidobacterium longum* subsp. *infantis* ATCC 15697 (BI_15697) and *Escherichia coli* ATCC 25922 (EC_25922) are purchased from China Industrial Microbiology Culture Collection Management Center (CICC).

Reducing Solution comprises: 10 g/L of bacterial peptone, 5 g/L of sodium chloride, 0.5 g/L of L-Cysteine H Cl, 1 mL/L of Tween 80 which are sterilized at 121° C. for 15 minutes. RB Agar Medium is prepared according to a method described by Hartemink[19] and sterilized at 118° C. for 15 minutes. MRSC Medium is prepared as follows: supplementing MRS broth medium with 0.5 g/L of L-Cysteine HCl, adding 15 g/L of agar for obtaining solid MRSC medium, and then sterilizing at 118° C. for 15 minutes.

No Carbon Source MRSC Medium comprises: 10 g/L of bacterial peptone, 5 g/L of yeast extract, 0.5 g/L of L-Cysteine HCl, 2 g/L of potassium dihydrogen phosphate, 5 g/L of anhydrous sodium acetate, 2 g/L of ammonium citrate, 0.2 g/L of magnesium sulfate heptahydrate, 0.05 g/L of manganese(II) sulfate monohydrate, 1 mL/L of Tween 80, which are sterilized at 118° C. for 15 minutes.

Different Carbon Source Media are prepared by: separately adding 2-fucosyllactose, short-chain galacto-oligosaccharides, galacto-oligosaccharides, glucose, and lactose to each of the Carbon Source MRSC Medium mentioned above, adjusting each final concentration to 10 g/L, and obtaining 2'-fucosyllactose medium, short-chain galacto-oligosaccharides medium, galacto-oligosaccharides medium, glucose medium, and lactose medium, which are sterilized at 118° C. for 15 minutes.

Embodiment 1: Isolation and Purification of *Bifidobacterium longum*

Use a sterile fecal collection device to collect fecal samples from breast-fed healthy infants in Harbin, Heilongjiang Province, China who are exclusively breastfed, full-term, delivered vaginally, aged within 6 months, and have not been introduced to solid foods or probiotic products within the past two weeks, immediately transfer collected fecal samples to a cooler with ice packs and transport the same to the laboratory, upon arrival at the laboratory, store the collected fecal samples in a −80° C. freezer, and perform isolation and purification experiment of bifidobacteria promptly as follows:

Take 1~2 grams of the collected fecal samples and perform a ten-fold serial dilution via a reducing solution, then prepare dilutions of $10^5$, $10^6$, and $10^7$, spread each dilution onto RB agar plates, place the RB agar plates in an anaerobic incubator set at 37° C., and incubate for 24~72 hours under anaerobic conditions.

After a designated incubation period, carefully examine the plates for the growth of distinct colonies. Select colonies that exhibit typical morphological characteristics for further analysis and purification.

After Obtaining Single Bacterial Colonies:

Pick a single bacterial colony and transfer the same to MRSC liquid medium, incubate the culture anaerobically at 37° C. for 24 hours, perform Gram straining and evaluate the strain for Gram-positive characteristics and negative catalase reaction, additionally, observe if the strain appears as rod-shaped or bifurcated, if a strain meets the criteria of being Gram-positive, catalase-negative, rod-shaped or bifurcated, streak the strain onto an agar plate in order to obtain isolated colonies, then repeat the above steps including picking single colonies, streaking, and incubating, until microscopic examination confirms the presence of pure cultures, assign each strain a unique identification number, add an equal volume of sterile glycerol (13% v/v) to the pure cultures, and store the strains at −20° C. in a freezer.

Inoculate a loopful of the strains from a preservation tube into MRSC liquid medium and incubate anaerobically at 37° C. for 24 hours, then, inoculate 1% (v/v) of the culture into MRSC liquid medium and continue anaerobic incubation for 18 hours as a reserve.

Use a scanning electron microscope (SEM) S-3400N equipped with a tungsten filament to observe bacterial morphology.

Generally, *bifidobacterium* observed under scanning electron microscope (SEM) exhibits a branching or rod-shaped morphology with irregular arrangement. Control strains BI_15697 and BI_M63 display smooth surfaces and appear as short rods or curved rods. However, strains BI_Y46 are more unique, as SEM images reveal a Y-shaped morphology, with the presence of flagella on surfaces of cells (see FIG. 1).

Use the Omega D4015-01 Bacterial Genomic DNA Extraction Kit from Omega Bio-Tek to extract bacterial genomic DNA, amplify extracted DNA by using specific primers for *Bifidobacterium* (Bif164-F:5'-GGGTGGTAATGCCGGATG-3'; PbiR2:5'-GAC-CATGCACCACCTGTGAA-3'), perform 1% agarose gel electrophoresis to verify amplification products and send the same to Shanghai Sangon Biotech Co., Ltd. for sequencing. After sequencing, obtain 16S rDNA sequence and compare the same on the BLAST website, revealing that *Bifidobacterium* BI_Y46 belongs to *Bifidobacterium longum* subsp. *infantis* (abbreviated as BI_Y46), which has been preserved at the China Center for Type Culture Collection (CCTCC) in Wuhan, with a preservation number of CCTCC NO: M 20221253, on Aug. 9, 2022.

Embodiment 2: Capability Evaluation of *Bifidobacterium longum* in Utilizing 2'-Fucosyllactose (2'-FL) and Short-Chain Galacto-Oligosaccharides Centrifuge 1 mL of BI_Y46, BI_15697, and BI_M63 bacterial solution cultured in MRSC medium at 10,000×g for 5 minutes at 4° C., discard the supernatant, wash the precipitate with 1 mL of sterile water, and re-suspend bacterial cells in 1 mL of sterile water.

Add 200 μL of 2'-fucosyllactose (2'-FL) medium, short-chain galacto-oligosaccharides medium, lactulose medium, glucose medium, and lactose medium into separate wells of a 96-well plate, inoculate each well with re-suspended bacterial cells at a 1% (v/v) inoculum size, make sure to record well numbers and set up following groups: control group. MRSC medium without a carbon source group, 2'-fucosyllactose medium group, short-chain galacto-oligosaccharides medium group, lactulose medium group, glucose medium group, lactose medium group, and MRSC medium without a carbon source with added bacteria group, incubate all groups anaerobically at 37° C., and measure absorbance values at 595 nm at 0 h, 24 h, and 48 h to evaluate capabilities in utilizing 2'-fucosyllactose and short-chain galacto-oligosaccharides.

The results show that *Bifidobacterium longum* subsp. *infantis* BI_Y46, along with the control strains BI_15697 and BI_M63, exhibited different metabolic capabilities towards 2'-fucosyllactose, short-chain galacto-oligosaccharides, galacto-oligosaccharides, glucose, and lactose, as shown in Table 1. Both BI_15697 and BI_Y46 demonstrate good utilization of glucose and lactose. The utilization ability of BI_Y46 for oligo-galactose is comparable to BI_M63 and superior to BI_15697. Moreover, BI_Y46 shows significantly stronger utilization abilities for short-chain oligo-galactose and 2'-fucosyllactose compared to BI_15697 and BI_M63. The results indicate that BI_Y46 has a stronger ability to utilize oligo-galactose compared to BI_15697, and additionally, BI_Y46 exhibits excellent utilization capabilities for human milk oligosaccharides such as 2'-fucosyllactose and galacto-oligosaccharides.

TABLE 1

Highest absorbance values (OD595 nm) of experimental strains within 48 hours of growth by separately using 2'-fucosyllactose, galacto-oligosaccharides, and short-chain galacto-oligosaccharides

| Strain | 2'-FL | SC-GOS | GOS | Glucose | Lactose |
|---|---|---|---|---|---|
| Bl_M63 | 0.65 ± 0.12b | 0.96 ± 0.05b | 1.27 ± 0.17a | 1.09 ± 0.17b | 1.27 ± 0.12b |
| Bl_15697 | 0.11 ± 0.03c | 0.25 ± 0.01c | 0.63 ± 0.03b | 1.36 ± 0.12ab | 1.36 ± 0.09ab |
| Y46 | 0.92 ± 0.11a | 1.05 ± 0.03a | 1.32 ± 0.11a | 1.54 ± 0.23a | 1.54 ± 0.16a |

Note:
different lower-case letters in the above form indicate a significant difference among different strains.

Embodiment 3: Probiotic Properties of Bifidobacteria

Extracellular Polysaccharide (EPS) Extraction and Determination:

Centrifuge the above bacterial solution at 6000×g for 10 minutes at 4° C., mix the supernatant with three times the volume of ethanol, precipitate at 4° C. for 16 hours, centrifuge the precipitate at 10000×g for 10 minutes at 4° C., after air-drying the precipitate, add 5 mL of water for re-suspending, dialyze the suspension with a 3.5 KD dialysis bag for 48 hours, change the water every 8 hours, and measure the extracellular polysaccharide (EPS) production by using the Alcian Blue method.

Add 50 μL of different concentrations of xanthan gum solutions to separate 1.5 mL EP tubes, then add 100 μL of 7% (v/v) ice-cold acetic acid and 100 μL of 0.5 mg/mL Alcian Blue, allow the reaction to proceed at room temperature for 30 minutes, then centrifuge at 6800×g for 5 minutes, take 200 μL of the supernatant, transfer to a 96-well plate, and measure absorbance values of the supernatant at 595 nm. Establish a standard curve equation and a cubic function equation based on the concentrations of xanthan gum solutions and the absorbance values.

Add 50 μL of the sample to a 1.5 mL EP tube, followed by adding 100 μL of 7% (v/v) ice-cold acetic acid and 100 μL of 0.5 mg/mL Alcian Blue. Allow the reaction to proceed at room temperature for 30 minutes, then centrifuge at 10,000×g for 5 minutes. Measure absorbance values of the supernatant at 595 nm. Use the method of standard curve analysis and perform a univariate solution to convert the absorbance values at 595 nm to milligrams of xanthan gum equivalent per milliliter.

Determination of Protein Content in Fermentation Broth and Surface Protein Content of Bacterial Cells:

Centrifuge 10 mL of the above bacterial solution at 6000×g for 10 minutes at 4° C., wash the precipitate twice with PBS, add 2 mL of a 5 mol/L solution of LiCl to the precipitate and incubate by constant shaking (200 r/min) for 1 hour at 37° C., centrifuge the mixture again at 6000×g for 10 minutes at 4° C. mix the supernatant with twice the volume of ice-cold acetone and place overnight at −20° C. and measure surface protein content of the bacterial cells by using the Bradford method.

Determination of Self-Aggregation Ability:

Centrifuge 5 mL of the above bacterial solution at 4500×g for 15 minutes at 4° C., wash the precipitate with PBS buffer and re-suspend, measure absorbance values of the bacterial suspension at 595 nm at 0 hour, 2 hours, 4 hours, and 6 hours. The aggregation rate (A %) can be calculated using the following formula:

$$A\% = (1 - At/A0) \times 100\%,$$

Where A0 is an initial absorbance value at 0 hours and At is a absorbance value at a specified time point.

Determination of Biofilm Formation Ability:

Centrifuge 1 mL of the above bacterial solution at 10,000×g for 5 minutes at 4° C., discard the supernatant, wash with 1 mL of sterile water, vortex thoroughly and centrifuge again at 10,000×g for 5 minutes at 4° C., and re-suspend the precipitate in 1 mL of sterile water. Add 200 uL of culture medium to each well of a 96-well plate, incubate at 37° C. under anaerobic conditions for 96 hours, remove the culture medium and wash each well with 200 uL of sterile water. Add 200 uL of 0.1% (w/v) crystal violet dye and incubate for 30 minutes, wash the wells again and allow them to air dry for 30 minutes, dissolve the cell-bound crystal violet by adding 200 uL of ethanol-acetone solution (80:20) and incubating for 10 minutes. Transfer 135 uL from each well to a new 96-well plate and measure absorbance values at 595 nm.

Simulated Gastric Fluid Tolerance Analysis

Inoculate the above bacterial solution into artificial gastric fluid at a volume ratio of 1:5 (gastric pepsin 10 g/L, adjusted to pH 2.0 with hydrochloric acid). Incubate at 37° C. without agitation. At 0 h, 0.5 h, and 3 h, perform serial dilutions of the bacterial suspension and plate the same on MRSC solid agar plates for colony counting.

Bile Salt Tolerance Analysis

Centrifuge 1 mL of the above bacterial solution at 10,000×g for 5 minutes at 4° C. Wash bacterial cells twice and re-suspend in MRSC culture medium containing 0.2% porcine bile salts. Incubate the suspension at 37° C. under anaerobic conditions. Perform colony counting respectively at 0 hour and 0.5 hours.

Determination of Bacteriostatic Ability of Cell-Free Supernatant:

Centrifuge 5 mL of the above bacterial culture at 10,000×g for 5 minutes at 4° C., collect the supernatant and filter the same through a 0.22 μm microporous membrane, and use EC_25922 (*Escherichia coli* strain) as an indicator strain and apply Oxford cup assay to assess the antibacterial activity of each bacterial strain.

All experiments were conducted independently 3 times, and the results are presented as the means±standard deviation ($\bar{x}$±SD). The experimental data were analyzed for statistical significance using the SPSS software with the Wald-Duncan test, with a significance level set at $P<0.05$, indicating a significant difference.

The present invention measured the extracellular polysaccharide content, bacterial surface protein content, biofilm formation, bile salt tolerance, inhibitory ability of cell-free supernatant against EC_25922 (as shown in Table 2), self-aggregation capacity of the BI_Y46 strain (as shown in Table 3), and simulated gastric fluid tolerance (as shown in Table 4) in comparison to control strains BI_15697 and BI_M63.

The results showed that the extracellular polysaccharide content of BI_Y46 was higher than that of the two control strains, but the difference was not significant. The bacterial surface protein content of BI_Y46 was significantly higher than that of the two control strains. Results from Table 1 indicated that BI_Y46 exhibited significantly higher tolerance to 0.2% pig bile salts compared to the control strains. Table 3 revealed that BI_Y46 demonstrated intermediate tolerance to gastric acid between BI_M63 and BI_15697. When using sterile MRSC medium as a control, the inhibitory ability of BI_Y46's cell-free supernatant against EC_25922 was comparable to BI_M63 but significantly higher than BI_15697. Furthermore, BI_Y46 exhibited significantly higher self-aggregation ability than the control strains,

TABLE 2

Comparison of different properties of experimental strains ($\bar{x}$ ± SD, n = 3)

| Item | Bl_M63 | Bl_15697 | Bl_Y46 |
|---|---|---|---|
| Exopolysaccharide content (mg/mL) | 0.36 ± 0.06a | 0.36 ± 0.03a | 0.44 ± 0.02a |
| Surface protein content of bacterial cells(mg/mL) | 0.27 ± 0.01b | 0.22 ± 0.02c | 0.31 ± 0.02a |
| Biofilm-forming capacity (OD595) | 0.11 ± 0.02a | 0.12 ± 0.03a | 0.11 ± 0.02a |
| 0.2% Porcine bile salt tolerance (Log reduction of bacterial colonies (CFU/mL)) | 7.68 ± 0.1b | 8.08 ± 0.11a | 7.25 ± 0.04c |
| Diameter of antibacterial ring (mm) | 13.50 ± 0.50a | 8.00 ± 0.00b | 12.83 ± 0.29a |

Note:
Different lower-case letters in the above form indicate a significant difference among different strains.

TABLE 3

Self-aggregation ability of each experimental strain ($\bar{x}$ ± SD, n = 3)

| Strain | 2 h (%) | 4 h (%) | 6 h (%) |
|---|---|---|---|
| Bl_M63 | 17.67 ± 2.74Cb | 27.37 ± 1.89Bb | 38.98 ± 0.96Ac |
| Bl_15697 | 18.92 ± 1.49Cb | 32.80 ± 3.82Bb | 48.43 ± 0.90Ab |
| Y46 | 30.56 ± 2.51Ca | 48.83 ± 5.76Ba | 68.56 ± 3.16Aa |

Note:
in the above form, capital letters indicate significant differences in growth conditions for a same strain at different time points, and lowercase letters indicate significant differences in growth conditions among different strains at a same time point.

TABLE 4

Simulated Gastric Tolerance at pH 2.0 ($\bar{x}$ ± SD, n = 3)

| Strain | 0 h (Log (CFU/mL)) | 0.5 h (Log (CFU/mL)) | 3 h (Log (CFU/mL)) |
|---|---|---|---|
| Bl_M63 | 7.08 ± 0.20Bb | 7.95 ± 0.02Aa | 8.23 ± 0.15Aa |
| Bl_15697 | 7.88 ± 0.02Aa | 6.09 ± 0.08Bc | 5.46 ± 0.28Cc |
| Bl_Y46 | 7.97 ± 0.02Aa | 7.76 ± 0.01Bb | 7.81 ± 0.03Bb |

Note:
in the above form, capital letters indicate significant differences in growth conditions for a same strain at different time points, and lowercase letters indicate significant differences in growth conditions among different strains at a same time point.

Embodiment 4: Determination of Cell Adhesion Capability

Colon cancer cells (HT-29) stored in the laboratory of the present invention are routinely cultured in a complete RPMI medium while changing medium every 2 days until a confluent monolayer is formed through cell fusion. To conduct adhesion experiments, an HT-29 monolayer is digested with trypsin and transferred to a 24-well tissue plate ($10^5$ cells per well). The cells are then cultured in a complete RPMI medium with 5% of $CO_2$ for 24 hours. Subsequently, the culture media is removed, and adherent HT-29 cells are washed twice with PBS. Then, 1 mL of antibiotic-free RPMI is added to each well. Overnight cultured bifidobacteria are diluted to obtain a bacterial suspension having a concentration of $10^7$ CFU/mL in the complete RPMI medium, the bacterial suspension is then added to the wells to achieve an initial infection ratio of 100:1 (bacteria: cells). The cells are incubated at 37° C. with 5% $CO_2$ for 0.5 hours. Afterward, the cells are washed twice with PBS buffer to remove non-adherent bacteria. To determine the number of adhered bacteria, the cells are treated with trypsin for 10 minutes. After centrifugation, the cell pellet is re-suspended in 1 mL of RPMI medium. Serial dilutions are performed, and the bacteria are counted by using plate counting method. The percentage of cell adhesion ability is defined as the number of adhered bacteria divided by the total number of inoculated bacteria, multiplied by 100%.

Figure 2:
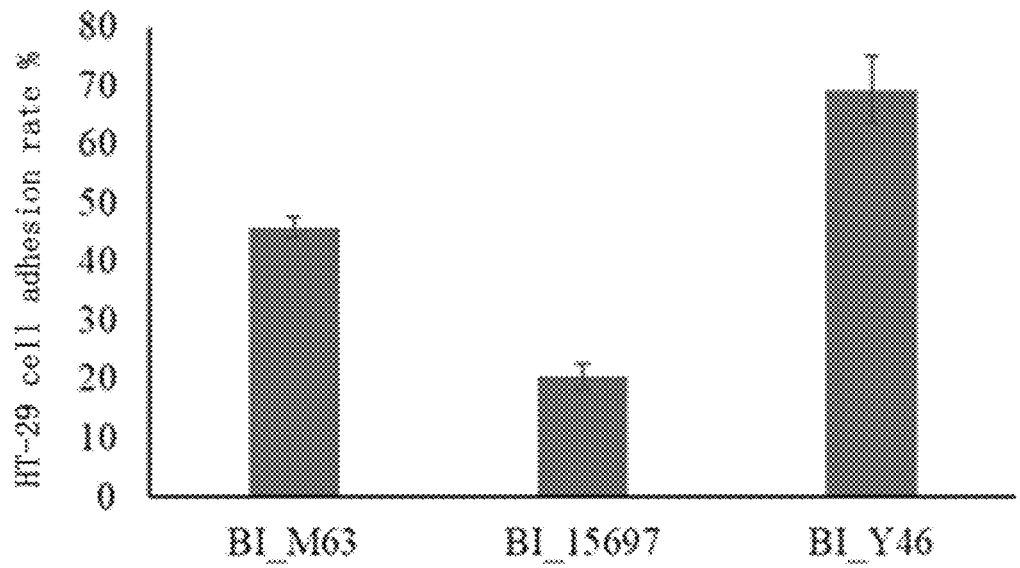
FIG. 2 shows adhesion ability of strains of *Bifidobacterium longum* subsp. *infantis* Y46 with fimbriae (BI_Y46) to HT-29 cells.

Adhesion to the gastrointestinal tract is considered a crucial prerequisite for bifidobacteria to colonize the human gut and exert its probiotic effects. In the present experiment, HT-29 colon cancer cells are used as a model to investigate the adhesion capacity of BI_Y46 strain compared to control strains on epithelial cells. The results (see FIG. 2) show that control strains BI_M63, BI_15697, and BI_Y46 all exhibited adhesion to HT-29 cells. However, BI_Y46 exhibited significantly higher cell adhesion capability compared to the two control strains. BI_Y46 had higher concentrations of surface proteins and self-aggregation ability than the control strains, and a structure called bacterial fimbriae is formed on surface of BI_Y46. The findings suggest that BI_Y46 possesses more adhesive proteins, which enhances its ability to adhere to intestinal epithelial cells. As a result, BI_Y46 can tightly bind to host epithelial cells, compete with pathogens for the same receptors, and replace pathogenic bacteria in host cells, thus playing a beneficial role in the host's gut health.

The above description are merely some embodiments of the present invention and do not limit the scope of the patent. Any equivalent modifications or applications in the relevant technical field, whether made directly or indirectly based on the content of this specification, are also included within the scope of patent protection of the present invention.

The invention claimed is:
1. A method for inhibiting *Escherichia coli*, comprising:
administering to a subject a product comprising a strain of *Bifidobacterium longum* subsp. *infantis* Y46 with fimbriae (BI_Y46) in an effective amount,
wherein the BI_Y46 is deposited in China Typical Culture Preservation Center, Wuhan, China, with an accession number of CCTCC NO: M 20221253, dated Aug. 9, 2022.

* * * * *

SEQUENCE LISTING

```
Sequence total quantity: 1
SEQ ID NO: 1              moltype = DNA  length = 1522
FEATURE                   Location/Qualifiers
source                    1..1522
                          mol_type = other DNA
                          organism = synthetic construct
SEQUENCE: 1
gtggagggtt cgattctggc tcaggatgaa cgctggcggc gtgcttaaca catgcaagtc  60
gaacgggatc catcaagctt gcttggtggt gagagtggcg aacgggtgag taatgcgtga 120
ccgacctgcc ccatacaccg gaatagctcc tggaaacggg tggtaatgcc ggatgttcca 180
gttgatcgca tggtcttctg ggaaagcttt cgcggtatgg gatggggtcg cgtcctatca 240
gcttgacggc ggggtaacgg cccaccgtgg cttcgacggg tagccggcct gagagggcga 300
ccggccacat tgggactgag atacggccca gactcctacg ggaggcagca gtggggaata 360
ttgcacaatg ggcgcaagcc tgatgcagcg acgccgcgtg agggatggag gccttcgggt 420
tgtaaacctc ttttatcggg gagcaagcgt gagtgagttt acccgttgaa taagcaccgg 480
ctaactacgt gccagcagcc gcggtaatac gtagggtgca agcgttatcc ggaattattg 540
ggcgtaaagg gctcgtaggc ggttcgtcgc gtccggtgtg aaagtccatc gcttaacggt 600
ggatccgcgc cgggtacggg cgggcttgag tgcggtaggg gagactggaa ttcccggtgt 660
aacggtggaa tgtgtagata tcgggaagaa caccaatggc gaaggcaggt ctctgggccg 720
ttactgacgc tgaggagcga aagcgtgggg agcgaacagg attagatacc ctggtagtcc 780
acgccgtaaa cggtggatgc tggatgtggg gcccgttcca cgggttccgt gtcggagcta 840
acgcgttaag catcccgcct ggggagtacg gccgcaaggc taaaactcaa agaaattgac 900
gggggcccgc acaagcggcg gagcatgcgg attaattcga tgcaacgcga agaaccttac 960
ctgggcttga catgttcccg acgatcccag agatggggtt tcccttcggg gcgggttcac 1020
aggtggtgca tggtcgtcgt cagctcgtgt cgtgagatgt tgggttaagt cccgcaacga 1080
gcgcaaccct cgccccgtgt tgccagcgga ttgtgccggg aactcacggg ggaccgccgg 1140
ggttaactcg gaggaaggtg gggatgacgt cagatcatca tgccccttac gtccagggct 1200
tcacgcatgc tacaatggcc ggtacaacgg gatgcgacgc ggcgacgcgg agcggatccc 1260
tgaaaaccgg tctcagttcg gatcgcagtc tgcaactcga ctgcgtgaag gcggagtcgc 1320
tagtaatcgc gaatcagcaa cgtcgcggtg aatgcgttcc cgggccttgt acacaccgcc 1380
cgtcaagtca tgaaagtggg cagcacccga agccggtggc ctaaccccett gtgggatgga 1440
gccgtctaag gtgaggctcg tgattgggac taagtcgtaa caaggtagcc gtaccggaag 1500
gtgcggctgg atcacctcct tt                                           1522
```